(12) United States Patent
Glock et al.

(10) Patent No.: US 6,569,806 B1
(45) Date of Patent: *May 27, 2003

(54) SELECTIVE HERBICIDAL COMPOSITION

(75) Inventors: Jutta Glock, Mumpf (CH); Manfred Hudetz, Rheinfelden (CH)

(73) Assignee: Syngenta Investment Corporation, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/819,014

(22) Filed: Mar. 17, 1997

Related U.S. Application Data

(63) Continuation of application No. 08/451,703, filed on May 26, 1995, now abandoned.

(30) Foreign Application Priority Data

Jun. 3, 1994 (CH) ............................................. 1758/94
Jul. 14, 1994 (CH) ............................................. 2253/94

(51) Int. Cl.$^7$ ........................ A01N 25/32; A01N 43/84; A01N 37/22
(52) U.S. Cl. ...................... 504/105; 504/130; 504/149; 504/342
(58) Field of Search ............................... 504/105, 130, 504/149, 342

(56) References Cited

U.S. PATENT DOCUMENTS

| | | | |
|---|---|---|---|
| 3,959,304 A | 5/1976 | Teach | 71/88 |
| 4,256,481 A | 3/1981 | Gardi et al. | 544/7 |
| 4,392,882 A | 7/1983 | Riebel et al. | 71/92 |
| 4,443,628 A | 4/1984 | Rinehart | 564/209 |
| 4,448,960 A | 5/1984 | Rohr et al. | 544/282 |
| 4,565,565 A | 1/1986 | Rohr et al. | 71/92 |
| 4,579,691 A | 4/1986 | Maier et al. | 558/159 |
| 4,618,361 A | 10/1986 | Moser | 47/57.6 |
| 4,676,823 A | 6/1987 | Maier et al. | 47/57.6 |
| 4,708,735 A | 11/1987 | Pallos et al. | 71/118 |
| 4,734,119 A | 3/1988 | Diel et al. | 558/154 |
| 4,739,093 A | 4/1988 | Diel et al. | 558/154 |
| 4,846,880 A | 7/1989 | Alt et al. | 546/146 |
| 4,897,109 A | 1/1990 | Martin | 560/9 |
| 4,971,618 A | 11/1990 | Pallos et al. | 71/93 |
| 5,002,606 A | 3/1991 | Moser et al. | 71/118 |
| 5,028,256 A | 7/1991 | Martin | 549/570 |
| 5,116,402 A | 5/1992 | Dutka et al. | 71/88 |
| 5,225,570 A | 7/1993 | Williams et al. | 546/275 |
| 5,256,625 A | 10/1993 | Bussler et al. | 504/107 |
| 5,981,432 A | * 11/1999 | Hudetz et al. | 504/105 |
| 6,063,732 A | 5/2000 | Ruegg | 504/140 |
| 6,159,899 A | 12/2000 | Hudetz et al. | 504/130 |

FOREIGN PATENT DOCUMENTS

| | | |
|---|---|---|
| DE | 2948535 | 6/1981 |
| EP | 0023305 | 2/1981 |
| EP | 0031686 | 7/1981 |
| EP | 0054278 | 6/1982 |
| EP | 0126710 | 11/1984 |
| EP | 0143078 | 5/1985 |
| EP | 0149974 | 7/1985 |
| EP | 0163607 | 12/1985 |
| EP | 0304409 | 2/1989 |
| FR | 2514611 | 4/1983 |

OTHER PUBLICATIONS

Rowe, L. Et Al., "Efficacy and Mode of Action of CGA–154281 . . . " Weed Science, vol. 39(1), pp. 78–82, Jan./Mar. 1991.*

Viger, P.R. Et Al., "Influence of Available Soil Water Content, Temperature, and CGA–154281 on Metolachlor Injury to Corn," Weed Science, vol. 39(2), pp. 227–231, Apr./Jun. 1991.*

Viger, P.R. Et Al., "Effects of CGA–154281 and Temperature on Metolachlor . . . " Weed Science, vol. 39(3), pp. 324–328, Jul./Sep. 1991.*

Chemical Abstract 99:117859X, vol. 99, 1983, p. 253.

Derwent Abstract 49641 K/21 of FR 2514611, Apr. 22, 1983.

The Pesticide Manual, 9$^{th}$ Ed., p. 61 (1991).

* cited by examiner

*Primary Examiner*—John Pak
(74) *Attorney, Agent, or Firm*—William A. Teoli, Jr.

(57) ABSTRACT

A mixture of a herbicidally effective amount of a haloacetamide of formula I

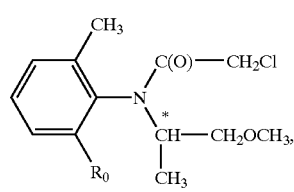

(I)

wherein $R_0$ is methyl or ethyl, and
to antagonise the herbicide, an antidotally effective amount of a compound of formula II as safener

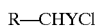

(II)

wherein R is a radical of formula

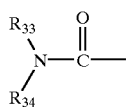

or R is a radical of formula

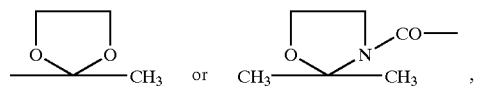

or R is a radical of formula

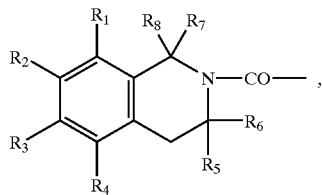

or R is a radical of formula

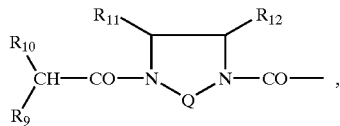

or R is a radical of formula

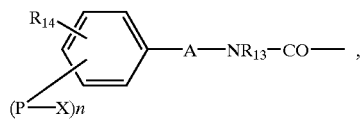

or R is a radical of formula $(H_5C_2O)_2P(O)CH_2NHCO-$ or

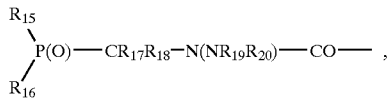

or R is a radical of formula

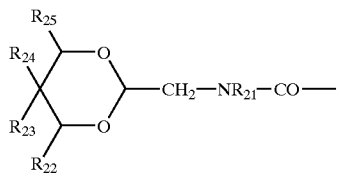

or of formula

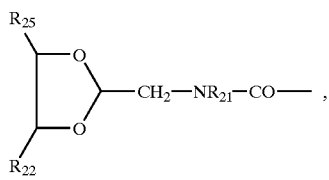

in each of which formulae the substituents are as defined in claim 1 and Y is chloro, or Y is hydrogen if R is a radical of formula $(H_5C_2O)_2P(O)CH_2NHCO-$, are very suitable for controlling weeds in crops of cultivated plants, in particular maize.

4 Claims, No Drawings

SELECTIVE HERBICIDAL COMPOSITION

This application is a continuation of application Ser. No. 08/451,703, filed May 26, 1995 now abandoned.

The present invention relates to a selective herbicidal composition for controlling grasses and weeds in crops of cultivated plants, especially in crops of maize, which composition comprises a herbicide and a safener (antidote) and protects the cultivated plants, but not the weeds, from the phytotoxic action of the herbicide, and to the use of said composition, or of the combination of herbicide and safener, for controlling weeds in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall.

To counteract this problem and similar ones, the proposal has already been made to use different compounds as safeners which are able to antagonise the harmful action of the herbicide on the cultivated plant, i.e. to protect the cultivated plant while leaving the herbicidal action on the weeds to be controlled virtually unimpaired. It has, however, been found that the proposed safeners often have a very species-specific action, not only with respect to the cultivated plants but also to the herbicide, and in some cases also subject to the mode of application, i.e. a specific safener will often be suitable only for a specific cultivated plant and a specific class of herbicide.

It has now been found that certain chloro- and dichloroacetamides are suitable for protecting cultivated plants from the phytotoxic action of the compound a RS,1'S(−)N-(1'-methyl-2'-methoxyethyl)-N-chloracetyl-2-ethyl-6-methylaniline of formula I

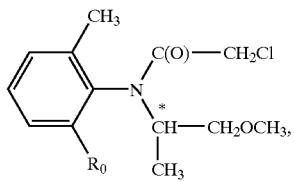

(I)

wherein $R_0$ is methyl or ethyl.

Accordingly, the invention provides a selective herbicidal composition comprising, in addition to conventional inert formulation assistants such as carriers, solvents and wetting agents, as active component, a mixture of
a) a herbicidally effective amount of a compound of formula I

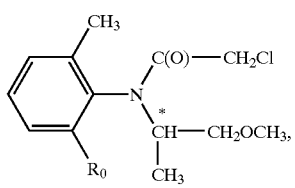

(I)

wherein $R_0$ is methyl or ethyl, and
b) to antagonise the herbicide, an antidotally effective amount of a compound of formula II as safener R—CHYCl (II)

wherein R is a radical of formula

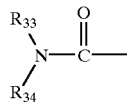

wherein
$R_{33}$ and $R_{34}$ are each independently of the other $C_1$–$C_6$alkyl or $C_2$–$C_6$alkenyl; or $R_{33}$ and $R_{34}$, taken together, are

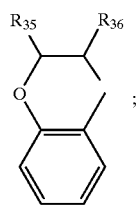

$R_{35}$ and $R_{36}$ are each independently of the other hydrogen or $C_1$–$C_6$alkyl;
or $R_{33}$ and $R_{34}$, taken together, are

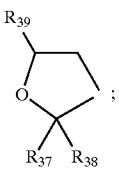

$R_{37}$ and $R_{38}$ are each independently of the other $C_1$–$C_4$alkyl, or $R_{37}$ and $R_{38}$, taken together, are —(CH$_2$)$_5$—;
$R_{39}$ is hydrogen, $C_1$–$C_4$alkyl or

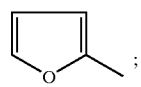

or $R_{33}$ and $R_{34}$, taken together, are

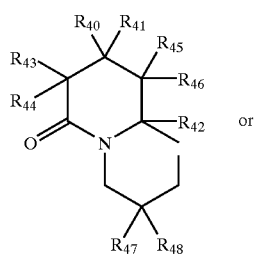

or

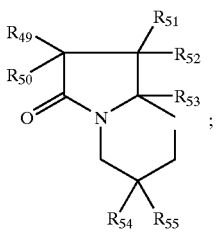

and $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{54}$ and $R_{55}$ are each independently of one another hydrogen or $C_1$–$C_4$alkyl, or R is a radical of formula

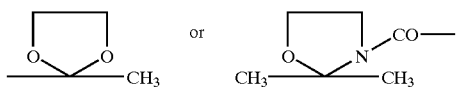

or R is a radical of formula

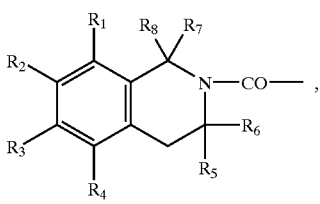

wherein $R_1$, $R_2$, $R_3$ and $R_4$ are each independently of one another hydrogen, $C_1$–$C_4$alkyl, $C_1$–$C_4$alkoxy or $C_1$–$C_4$haloalkyl, $R_5$, $R_6$, $R_7$ and $R_8$ are each independently of one another hydrogen, $C_1$–$C_4$alkyl or $C_1$–$C_4$haloalkyl, or R is a radical of formula

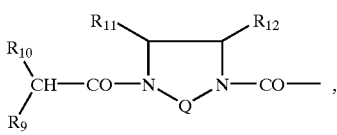

wherein $R_9$ is $C_1$–$C_4$alkyl or halogen, $R_{10}$ is halogen, $R_{11}$ and $R_{12}$ are each independently of the other hydrogen or $C_1$–$C_4$alkyl, and Q is $C_1$–$C_4$alkylene or alkyl-substituted $C_1$–$C_4$alkylene, or R is a radical of formula

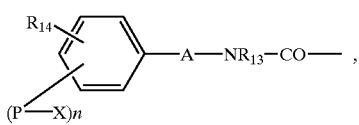

wherein $R_{14}$ is hydrogen, halogen, $C_1$–$C_4$alkyl, dioxymethylene, $C_1$–$C_4$alkoxy, $C_2$–$C_4$alkenyloxy, $C_2$–$C_4$alkynyloxy or cyano-$C_1$–$C_4$alkyl, P is $C_1$–$C_4$alkyl, $C_2$–$C_4$alkenyl, $C_2$–$C_4$alkynyl, $C_3$–$C_8$cycloalkyl, $C_1$–$C_4$alkoxy-$C_1$–$C_4$alkyl, $C_2$–$C_4$alkenoxy-$C_1$–$C_4$alkyl, $C_2$–$C_4$alkynoxy-$C_1$–$C_4$alkyl, $C_1$–$C_4$alkylthio-$C_1$–$C_4$alkyl, $C_2$–$C_4$alkenylthio-$C_1$–$C_4$alkyl, $C_2$–$C_4$alkynylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, halo-$C_1$–$C_4$alkyl, cyano-$C_1$–$C_4$alkyl, 2,2-di-$C_1$–$C_4$alkoxy-$C_1$–$C_4$alkyl, 1,3-dioxolan-2-yl-$C_1$–$C_4$alkyl, 1,3-dioxolan-4-yl-$C_1$–$C_4$alkyl, 2,2-di-$C_1$–$C_4$alkyl-1,3-dioxolan-4-yl-$C_1$–$C_4$alkyl, 1,3-dioxan-2-yl-$C_1$–$C_4$alkyl, 2-benzopyranyl-$C_1$–$C_4$alkyl, $C_1$–$C_4$alkoxycarbonyl or $C_2$–$C_4$alkenyloxycarbonyl or tetrahydrofurfuryl-$C_1$–$C_4$alkyl, the group P-X is also halo-$C_1$–$C_4$alkyl, X is O, S, SO or $SO_2$, n is 1, 2 or 3, A is a $C_1$–$C_8$hydrocarbon radical or a $C_1$–$C_8$hydrocarbon radical which is substituted by alkoxy, alkylthio, fluoro, cyano or haloalkyl, and $R_{13}$ is hydrogen, a $C_1$–$C_5$hydrocarbon radical or a $C_1$–$C_5$hydrocarbon radical which is substituted by alkoxy, polyalkoxy, halogen, cyano or trifluoromethyl;

$C_3$–$C_8$cycloalkyl, $C_1$–$C_4$alkyl-$C_3$–$C_8$cycloalkyl, di-$C_1$–$C_4$alkoxy-$C_1$–$C_4$alkyl, 1,3-dioxolan-2-yl-$C_1$–$C_4$alkyl, 1,3-dioxolan-4-yl-$C_1$–$C_4$alkyl, 1,3-dioxan-2-yl-$C_1$–$C_4$alkyl, furyl-$C_1$–$C_4$alkyl, tetrahydrofuryl-$C_1$–$C_4$alkyl, or a radical of formula —$NHCO_2R_{01}$, —$CH_2CO_2R_{01}$, —$CH(CH_3)CO_2R_{01}$ or —$CH(R_{02})$—$C(R_{03})$=$NOR_{04}$, wherein $R_{01}$ is methyl, ethyl, propyl, isopropyl or allyl, $R_{02}$ and $R_{03}$ are each hydrogen or $C_1$–$C_4$alkyl, and $R_{04}$ is hydrogen, $C_1$–$C_4$alkyl, $C_2$–$C_4$alkenyl or $C_2$–$C_4$alkynyl, or R is a radical of formula $(H_5C_2O)_2P(O)CH_2NHCO$— or

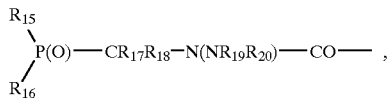

wherein $R_{15}$ and $R_{16}$ are each independently of the other hydroxyl, $C_1$–$C_4$alkyl, aryl, $C_1$–$C_4$alkoxy, $C_2$–$C_4$alkenyloxy, $C_2$–$C_4$alkynyloxy, $C_2$–$C_4$haloalkoxy, $C_2$–$C_8$alkoxyalkoxy, $C_1$–$C_4$cyanoalkoxy, $C_1$–$C_4$phenylalkoxy or aryloxy or aryloxy which is substituted by halogen, cyano, nitro or $C_1$–$C_4$alkoxy, $R_{17}$ is hydrogen, $C_1$–$C_4$alkyl or phenyl, or phenyl which is substituted by halogen, cyano, nitro or $C_1$–$C_4$alkoxy, $R_{18}$ is hydrogen, or $C_1$–$C_4$alkyl, $R_{19}$ is hydrogen or a radical of formula —$COCX_1X_2$—$R_{06}$, or an alkenoyl radical which contains 2 to 4 carbon atoms in the alkenyl moiety and which is substituted by halogen, and $X_1$ and $X_2$ are each independently of the other hydrogen or halogen, or is a radical of formula —$COOR_{07}$ or —$COR_{08}$ or a $C_1$–$C_4$alkyl, $C_2$–$C_4$alkenyl or $C_1$–$C_4$phenylalkyl radical which may be substituted at the phenyl ring by halogen, cyano, nitro or $C_1$–$C_4$alkoxy, and $R_{20}$ is hydrogen, $C_1$–$C_4$alkyl, $C_2$–$C_4$alkenyl or $C_2$–$C_4$alkynyl, $R_{06}$ is hydrogen, halogen or $C_1$–$C_6$alkyl, $R_{07}$ is $C_1$–$C_4$alkyl, $C_1$–$C_4$phenylalkyl or $C_1$–$C_4$phenylalkyl which is substituted in the phenyl moiety by halogen, cyano, nitro or $C_1$–$C_4$alkoxy, and $R_{08}$ is $C_1$–$C_4$alkyl, $C_2$–$C_4$alkenyl, $C_2$–$C_4$alkynyl, phenyl, $C_1$–$C_4$phenylalkyl or $C_1$–$C_4$phenylalkyl which is substituted in the phenyl moiety by halogen, cyano, nitro or $C_1$–$C_4$alkoxy, or R is a radical of formula

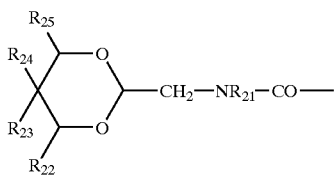

or of formula

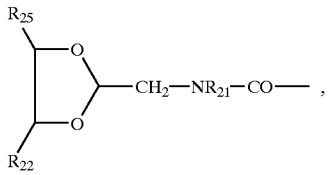

wherein $R_{21}$ is methyl, ethyl, propyl, 1-methylethyl, 2-propenyl, 2-butenyl, 1,1-dimethyl-2-propenyl, 2-propynyl or 2-methyl-2-propynyl, and $R_{22}$, $R_{23}$, $R_{24}$ and $R_{25}$ are each independently of one another hydrogen or methyl, and Y is chloro, or Y is hydrogen if R is a radical of formula $(H_5C_2O)_2P(O)CH_2NHCO—$.

The alkyl groups cited in connection with the compounds of formula II may be straight-chain or branched and are typically methyl, ethyl, propyl, butyl, pentyl and hexyl, as well as branched isomers thereof. Suitable alkenyl radicals are derived from the aforementioned alkyl radicals. Aryloxy is most suitably phenyl and naphthoxy. Hydrocarbon radicals will be understood as meaning monovalent or divalent, saturated or unsaturated straight-chain or branched, or saturated or unsaturated cyclic radicals of carbon and hydrogen, typically alkyl, cycloalkyl, alkenyl, alkynyl, cycloalkenyl and phenyl.

The invention further relates to the use of the novel composition for controlling weeds and grasses in crops of cultivated plants, in particular maize.

Preferred compounds of formula II for use in the novel composition are those wherein R is a radical of formula

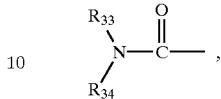

wherein $R_{33}$ and $R_{34}$ together are

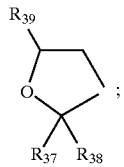

$R_{37}$ and $R_{38}$ are each independently of the other $C_1$–$C_4$alkyl; or $R_{37}$ and $R_{38}$, taken together, are $—(CH_2)_5—$; and $R_{39}$ is hydrogen, $C_1$–$C_4$alkyl or

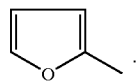

Examples of particularly suitable compounds of formula II are listed in the following Tables 1 and 2.

TABLE 1

Compounds of formula II (II)

| Cmpd. No. | $R_{33}$ | $R_{34}$ | $R_{33} + R_{34}$ |
|---|---|---|---|
| 1.001 | $CH_2=CHCH_2$ | $CH_2=CHCH_2$ | — |
| 1.002 | — | — | ![tetrahydrofuran with two CH3] |
| 1.003 | — | — | ![methyl-substituted tetrahydrofuran with two CH3] |

TABLE 1-continued

Compounds of formula II (II)

$$\underset{R_{34}}{\overset{R_{33}}{N}}-\overset{O}{\underset{\|}{C}}-CHCl_2$$

| Cmpd. No. | $R_{33}$ | $R_{34}$ | $R_{33} + R_{34}$ |
|---|---|---|---|
| 1.004 | — | — | 1-oxaspiro[4.5]decane |
| 1.005 | — | — | 2-(furan-2-yl)-2,2-dimethyl-1,3-dioxolane-like structure |
| 1.006 | — | — | 2-isopropyl-chroman derivative |
| 1.007 | — | — | bicyclic pyrrolidinone with gem-dimethyl groups |
| 1.008 | — | — | 1,4-dioxaspiro[4.5]decane |
| 1.009 | — | — | 1-methyl-1,2,3,4-tetrahydronaphthalene |
| 1.010 | 1,3-dioxolan-2-yl-CH$_2$CH$_2$— | CH$_2$=CHCH$_2$ | — |
| 1.011 | 3,4-dimethoxybenzyl— | (CH$_3$)$_2$CH— | — |

TABLE 2

Compounds of formula II 2.1     $(C_2H_5O)_2P(O)—CH_2NHCO—CH_2—Cl$ 2.2 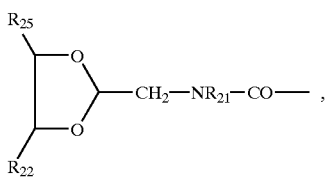

Another group of preferred compounds of formula II comprises those compounds wherein R is a radical of formula

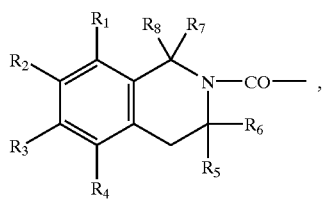

wherein $R_{21}$ is methyl, ethyl, propyl, 2-propenyl or 2-butenyl, and $R_{22}$ and $R_{25}$ are hydrogen. Among this group of compounds, that compound is particularly preferred wherein $R_{21}$ is 2-propenyl.

Further preferred compounds of formula II are those wherein R is a radical of formula

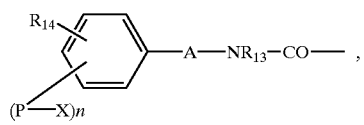

wherein $R_1$ to $R_8$ are each independently of one another hydrogen or $C_1$–$C_4$alkyl. Those compounds are particularly suitable wherein $R_1$ to $R_7$ are hydrogen and $R_8$ is methyl.

In another group of particularly suitable compounds R is a radical of formula

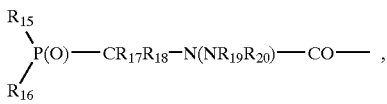

wherein $R_{14}$ is hydrogen, $C_1$–$C_4$alkyl or $C_1$–$C_4$alkoxy, P is $C_1$–$C_4$alkyl, $C_2$–$C_4$alkenyl or $C_2$–$C_4$alkynyl, X is O or S, n is 1, A is a $C_1$–$C_8$hydrocarbon radical and $R_{13}$ is hydrogen or a $C_1$–$C_5$hydrocarbon radical. Among this group of compounds, those compounds of formula II are particularly suitable wherein $R_{14}$ is $C_1$–$C_4$alkoxy, P is $C_1$–$C_4$alkyl, X is O, A is $C_1$–$C_4$alkylene and $R_{13}$ is $C_1$–$C_4$alkyl. The compound in which $R_{14}$ is methoxy, P is methyl, A is methylene and $R_{13}$ is isopropyl is of particular interest.

A further group of preferred compounds of formula II is that wherein R is a radical of formula

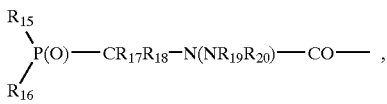

wherein $R_{15}$ and $R_{16}$ are each independently of the other hydroxyl, $C_1$–$C_4$alkyl or $C_1$–$C_4$alkoxy, $R_{17}$ and $R_{18}$ are each independently of the other hydrogen or $C_1$–$C_4$alkyl, and $R_{19}$ is hydrogen or a radical of formula —$COOR_{07}$, wherein $R_{07}$ is $C_1$–$C_4$alkyl, and $R_{20}$ is hydrogen or $C_1$–$C_4$alkyl. Most preferably $R_{16}$ and $R_{15}$ are $C_1$–$C_4$alkoxy, $R_{17}$ and $R_{18}$ are hydrogen, $R_{19}$ is a radical of formula —$COOR_{07}$, wherein $R_{07}$ is $C_1$–$C_4$alkyl, and $R_{20}$ is hydrogen. The compound wherein $R_{15}$ and $R_{16}$ are isopropoxy and $R_{19}$ is —$COOC_2H_5$ is of particular importance.

Particularly suitable compositions contain, as compound of formula II, a compound of formula III

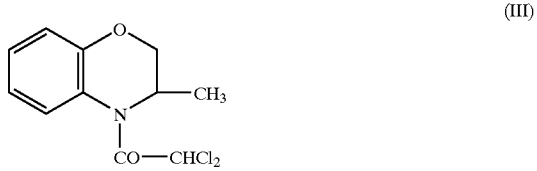

or of formula IV

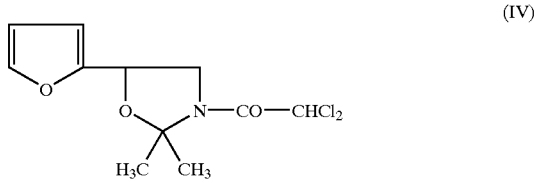

or of formula V

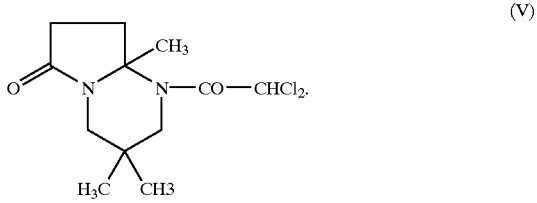

The compound of formula I used in the practice of this invention and the preparation thereof is described, inter alia, in U.S. Pat. No. 5,002,606. The compounds of formula II used in the novel compositions and the preparation thereof are disclosed inter alia, in U.S. Pat. No. 4,971,618, U.S. Pat. No. 3,959,304, U.S. Pat. No. 4,256,481, U.S. Pat. No. 4,708,735, EP-A-149 974, EP-A-304 409, EP-A-31 686, EP-A-54 278, EP-A-23 305, U.S. Pat. No. 4,846,880, EP-A-143 078, EP-A-163 607, EP-A-126 710, as well as in DE-A-2 948 535.

The invention also relates to a method of selectively controlling weeds in crops of cultivated plants, which comprises treating said cultivated plants, the seeds or seedlings or the crop area thereof, concurrently or separately, with a herbicidally effective amount of the compound of formula I and, to antagonise the herbicide, an antidotally effective amount of a compound of formula II.

Suitable cultivated plants which can be protected by the compounds of formula II against the harmful action of the aforementioned herbicide are preferably those important in the food or textile sector, typically sugar cane and, in particular, millet and maize, as well as rice and other varieties of cereals such as wheat, rye, barley and oats.

The weeds to be controlled may be monocot as well as dicot weeds.

Crop areas are the areas already under cultivation with the crop plants or seeds thereof, as well as the areas intended for cultivation with said crop plants.

Depending on the end use, a safener of formula II can be used for pretreating seeds of the crop plants (dressing of seeds or seedlings) or it can be incorporated in the soil before or after sowing. It can, however, also be applied by itself alone or together with the herbicide pre- or postemergence. Treatment of the plant or the seeds with the safener can therefore in principle be carried out irrespective of the time of application of the phytotoxic chemical. Treatment of the plant can, however, also be carried out by simultaneous application of the phytotoxic chemical and safener (tank mixture).

The concentration of safener to be applied with respect to the herbicide will depend substantially on the mode of application. Where a field treatment is carried out either by using a tank mixture with a combination of safener and herbicide or by separate application of safener and herbicide, the ratio of safener to herbicide will usually be from 1:100 to 1:1, preferably from 1:50 to 1:10.

In field treatment, 0.001 to 5.0 kg/ha, preferably 0.001 to 0.5 kg/ha, of safener, will usually be applied.

The concentration of herbicide is usually in the range from 0.001 to 10 kg/ha, but will preferably be from 0.005 to 5 kg/ha.

The novel compositions are suitable for all methods of application commonly employed in agriculture, including preemergence application, postemergence application and seed dressing.

For seed dressing, 0.001 to 10 g of safener/kg of seeds, preferably 0.05 to 2 g of safener/kg of seeds, will usually be applied. If the safener is used in liquid form shortly before sowing to effect soaking, then it is preferred to use safener solutions that contain the active ingredient in a concentration of 1 to 10 000 ppm, preferably of 100 to 1000 ppm.

For application, it is preferred to process the compounds of formula II, or combinations of the compounds of formula II and the herbicides of formula I, together with the assistants conventionally employed in formulation technology, typically to emulsifiable concentrates, coatable pastes, directly sprayable or dilutable solutions, dilute emulsions, wettable powders, soluble powders, dusts, granulates or microcapsules.

The formulations are prepared in known manner, e.g. by homogeneously mixing and/or grinding the active ingredients with extenders, typically with solvents or solid carriers. Surface-active compounds (surfactants) can additionally be used for preparing the formulations.

Suitable solvents may typically be: aromatic hydrocarbons, preferably the fractions containing 8 to 12 carbon atoms, for example xylene mixtures or substituted naphthalenes; phthalates such as dibutyl or dioctyl phthalate; aliphatic hydrocarbons such as cyclohexane or paraffins; alcohols and glycols and their ethers and esters, for example ethanol, ethylene glycol, 2-methoxyethanol or 2-ethoxyethanol; ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soybean oil; or water.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residues.

Depending on the safener, and usually also on the herbicide, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of mixtures of natural fatty acids which can be obtained, inter alia, from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl) ethylammonium bromide.

The surfactants customarily employed in the art of formulation are described, inter alia, in "Mc Cutcheon's Detergents and Emulsifiers Annual", MC Publishing Corp., Glen Rock, N.J., 1981, H. Stache, "Tensid-Taschenbuch" (Handbook of Surfactants), Carl Hanser Verlag, Munich/Vienna 1981, and J. Ash, "Encyclopedia of Surfactants", Vol. I–III, Chemical Publishing Co., New York, 1980–81.

The agrochemical formulations will usually contain from 0.1 to 99% by weight, preferably from 0.1 to 95% by weight, of safener of formula II or mixture of safener and herbicide, from 1 to 99.9% by weight, preferably from 5 to 99.8% by weight, of a solid or liquid formulation assistant, and from 0 to 25% by weight, preferably from 0.1 to 25% by weight, of a surfactant.

Whereas it is preferred to formulate commercial products as concentrates, the end user will normally use dilute formulations.

The compositions may also contain further ingredients such as stabilisers, antifoams, viscosity regulators, binders, tackifiers, as well as fertilisers or other chemical agents, e.g. commercial chloroacetanilides such as Frontier, Metazachlor, Acetochlor, Alachlor, Metolachlor or Butachlor, for achieving special effects.

Different methods and techniques may suitably be used for applying compounds of formula II or compositions containing them for protecting cultivated plants from the harmful effects of the herbicide of formula I, typically the following:

i) Seed Dressing a) Dressing the seeds with a wettable powder formulation of the compound of formula II by shaking in a vessel until the safener is uniformly distributed on the surface of the seeds (dry treatment), using up to c. 1 to 500 g of compound of formula II (4 g to 2 kg of wettable powder) per 100 kg of seeds.

b) Dressing seeds with an emulsifiable concentrate of the compound of formula II by method a) (wet treatment).

c) Dressing by immersing the seeds in a mixture containing 100–1000 ppm of compound of formula II for 1 to 72 hours, leaving them wet or subsequently drying them (seed soaking).

Seed dressing or treatment of the germinated seedlings are naturally the preferred methods of application, as the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, plus or minus deviations from the indicated limiting concentrations are possible (repeat dressing).

ii) Application From a Tank Mixture

A liquid formulation of a mixture of safener and herbicide (reciprocal ratio from 10:1 to 1:100) is used, the concentration of herbicide being from 0.01 to 10 kg/ha. This tank mixture is applied before or after sowing.

iii) Application in the Furrow

The safener formulated as emulsifiable concentrate, wettable powder or granulate is applied to the open furrow in which the seeds have been sown. After covering the furrow, the herbicide is applied preemergence in conventional manner.

iv) Controlled Release of Safener

A solution of the compound of formula II is applied to mineral granulate substrates or polymerised granulates (urea/formaldehyde) and allowed to dry. A coating may additionally be applied (coated granulates) which permits controlled release of the safener over a specific period of time.

The following examples illustrate the activity of the novel compositions in more detail.

Formulation Examples for Mixtures of the
Compound of Formula I and a Safener of Formula
II (Throughout, Percentages are by Weight)

| F1. Emulsifiable concentrates | a) | b) | c) | d) |
|---|---|---|---|---|
| compound mixture | 5% | 10% | 25% | 50% |
| Ca dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$—$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| compound mixture | 5% | 10% | 50% | 90% |
| 1-methoxy-3-(3-methoxypropoxy)-propane | — | 20% | 20% | — |
| polyethylene glycol 400 | 20% | 10% | — | — |
| N-methyl-2-pyrrolidone | — | — | 30% | 10% |
| mixture of aromatic hydrocarbons $C_9$—$C_{12}$ | 75% | 60% | — | — |

The solutions are suitable for use as microdrops.

| F3. Wettable powders | a) | b) | c) | d) |
|---|---|---|---|---|
| compound mixture | 5% | 25% | 50% | 80% |
| sodium ligninsulfonate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound mixture is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| compound mixture | 0.1% | 5% | 15% |
| highly dispersed silica | 0.9% | 2% | 2% |
| inorganic carrier (Ø 0.1–1 mm) e.g. CaCO₃ or SiO₂ | 99.0% | 93% | 83% |

The compound mixture is dissolved in methylene chloride, the solution is sprayed on to the carrier, and the solvent is removed under vacuum.

| F5. Coated granulates | a) | b) | c) |
|---|---|---|---|
| compound mixture | 0.1% | 5% | 15% |
| polyethylene glycol 200 | 1.0% | 2% | 3% |
| highly dispersed silica | 0.9% | 1% | 2% |
| inorganic carrier (Ø 0.1–1 mm) e.g. CaCO₃ or SiO₂ | 98.0% | 92% | 80% |

The finely ground compound mixture is uniformly applied in a mixer to the kaolin moistened with polyethylene glycol. Non-dusty coated granulates are obtained in this manner.

| F6. Extruder granulates | a) | b) | c) | d) |
|---|---|---|---|---|
| compound mixture | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound mixture is mixed with the adjuvants and the mixture is moistened with water. This mixture is extruded and then dried in a stream of air.

| F7. Dusts | a) | b) | c) |
|---|---|---|---|
| compound mixture | 0.1% | 1% | 5% |
| talcum | 39.9% | 49% | 35% |
| kaolin | 60.0% | 50% | 60% |

Ready for use dusts are obtained by mixing the compound mixture with the carriers and milling the mixture so obtained on a suitable mill.

| F8. Suspension concentrates | a) | b) | c) | d) |
|---|---|---|---|---|
| compound mixture | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is intimately mixed with the adjuvants to give a suspension concentrate from which suspensions of any desired concentration can be prepared by dilution with water.

Example B1

Preemergence Phytoxic Action of the Herbicide of Formula I and of the Mixtures of Herbicide and Safener of Formula II on Maize Maize is sown in standard soil in plastic pots. Immediately after sowing, the pots are sprayed with an aqueous suspension of the test substances (500 l of water/ha) prepared from one of the above formulations 1 to 8. The concentration of herbicide of formula I is 4000, 3000 and 2000 g/ha. The safener No. 1.006 is applied in a ratio to the herbicide of 1:18, 1:24 and 1:30. The test plants are afterwards cultivated in a greenhouse under optimum conditions. The phytotoxic action of the herbicide on the maize (percentage phytotoxicity) is evaluated after a test duration of 22 days.

| Ratio of herbicide to safener | % Phytotoxicity |
|---|---|
| a) Concentration of herbicide: 4000 g/ha | |
| no safener | 65 |
| 18:1 | 20 |
| 24:1 | 20 |
| 30:1 | 15 |
| b) Concentration of herbicide: 3000 g/ha | |
| no safener | 55 |
| 18:1 | 0 |
| 24:1 | 0 |
| 30:1 | 0 |
| c) Concentration of herbicide: 2000 g/ha | |
| no safener | 25 |
| 18:1 | 0 |
| 24:1 | 0 |
| 30:1 | 0 |

The results show that the compounds of formula II are able to reduce markedly the damage caused by the herbicide to the cultivated plants.

What is claimed is:

1. A composition for the selective control of weeds in crops of cultivated plants, comprising, in addition to inert carriers and adjuvants, as active component, a mixture of a) a herbicidally effective amount of an αRS,1'S(-)N (1'methyl-2'-methoxyethyl-N-chloracetyl-2-ethyl-6-methylaniline diastereomeric pair of compounds of formula I

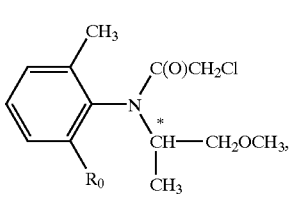

(I)

wherein $R_0$ is ethyl and b) to antagonize the herbicide, an antidotally effective amount of a compound of formula III as safener

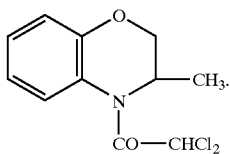

2. A method of selectively controlling weeds and grasses in crops of cultivated plants, which comprises treating said plants, the seeds or the locus thereof, concurrently or separately, with an effective amount of an αRS,1'S(−)N (1'methyl-2'-methoxyethyl-N-chloracetyl-2-ethyl-6-methylaniline diastereomeric pair of compounds of formula I

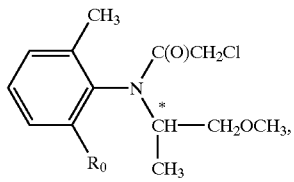

wherein $R_0$ is ethyl and, to antagonize the herbicide, an antidotally effective amount of a compound of formula III as safener

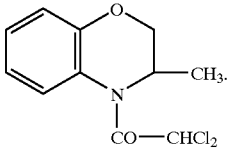

3. A method according to claim 2, wherein the plants, the seeds or the locus thereof is treated with 0.001 to 10 kg/ha of the diastereomeric pair of compounds of formula I and 0.005 to 0.5 kg/ha of a compound of formula III.

4. A method according to claim 2, wherein the cultivated plants are maize.

* * * * *